US008471011B2

(12) United States Patent
Rey et al.

(10) Patent No.: US 8,471,011 B2
(45) Date of Patent: Jun. 25, 2013

(54) PREPARATION OF ACID ADDITION SALTS OF AMINE BASES BY SOLID PHASE—GAS PHASE REACTIONS

(75) Inventors: Allan W. Rey, Brantford (CA); Lotfi Derdour, Brantford (CA); K. S. Keshava Murthy, Ancaster (CA); Probal Kanti Datta, Brantford (CA); Martin Ehlert, Branchton (CA); Stephen E. Horne, Burlington (CA)

(73) Assignee: Apotex PharmaChem Inc., Brantford (CA)

( * ) Notice: Subject to any disclaimer, the term of this patent is extended or adjusted under 35 U.S.C. 154(b) by 1711 days.

(21) Appl. No.: 11/168,523

(22) Filed: Jun. 29, 2005

(65) Prior Publication Data
US 2006/0205944 A1 Sep. 14, 2006

(30) Foreign Application Priority Data
Mar. 11, 2005 (CA) .................................... 2500676

(51) Int. Cl.
*C07D 239/72* (2006.01)
(52) U.S. Cl.
USPC ........................................................ 544/291
(58) Field of Classification Search
USPC ........... 544/284, 291; 546/199, 229; 549/491; 514/252.17
See application file for complete search history.

(56) References Cited

U.S. PATENT DOCUMENTS

| | | | | |
|---|---|---|---|---|
| 4,013,670 A | * | 3/1977 | Banitt et al. | 546/309 |
| 4,026,894 A | * | 5/1977 | Winn et al. | 544/291 |
| 4,066,772 A | * | 1/1978 | Vandenberk et al. | 514/278 |
| 4,831,031 A | * | 5/1989 | Lowe et al. | 514/254.02 |
| 4,927,936 A | * | 5/1990 | Crossley et al. | 546/181 |
| 5,047,548 A | * | 9/1991 | Richardson et al. | 548/267.6 |
| 5,240,935 A | * | 8/1993 | DeHaven-Hudkins et al. | 514/295 |
| 6,630,568 B1 | * | 10/2003 | Johnson et al. | 528/486 |
| 2005/0256139 A1 | | 11/2005 | Zetina-Rocha et al. | |

FOREIGN PATENT DOCUMENTS

| | | | |
|---|---|---|---|
| CA | 2471219 | | 12/2005 |
| GB | 1565966 | * | 4/1980 |

OTHER PUBLICATIONS

Berthelot, M.P.E., Comptes Rendus Hebdomadaires des Seances de l'Academie des Sciences, 1899, vol. 129, pp. 687-694.*
English Translation, Berthelot M., "Research on Diamines. Diethylenediamine (Piperazine)", McElroy Translation Company, Jun. 2009.*
Csep, "The Earth's Atmosphere", astr161, Apr. 7, 2011, http://csep10.phys.utk.edu/astr161/lect/earth/atmosphere.html.*
Kaupp G Cryst Eng Comm 5(23) 117-133 (2003).
Kaupp G et al Gas Solid reactions with Acetone Chem Ber vol. 127 2249-2261 (1994).
Kaupp G et al Water free solid state synthesis quantitative yield Chemosphere vol. 43 pp. 55-61 (2001).
Kaupp G Gas-Solid-reactions with sulfur compounds Phosphorus sulfur and silicon vol. 53 pp. 109-120 (1990).
Kaupp G et al Mol Cryst Liq Cryst vol. 313 361-366 (1998).
Tanaka Chem Rev 100 1025-1074 (2000).

* cited by examiner

*Primary Examiner* — Paul V. Ward

(57) ABSTRACT

A process for the preparation of an acid addition salt of an organic base comprising exposing the organic base in solid form to a gaseous acid, with the proviso that ziprasidone, its acid addition salts and intermediates thereof are excluded.

23 Claims, 1 Drawing Sheet

Figure 1. PXRD Diffractogram of Domperidone Hydrochloride
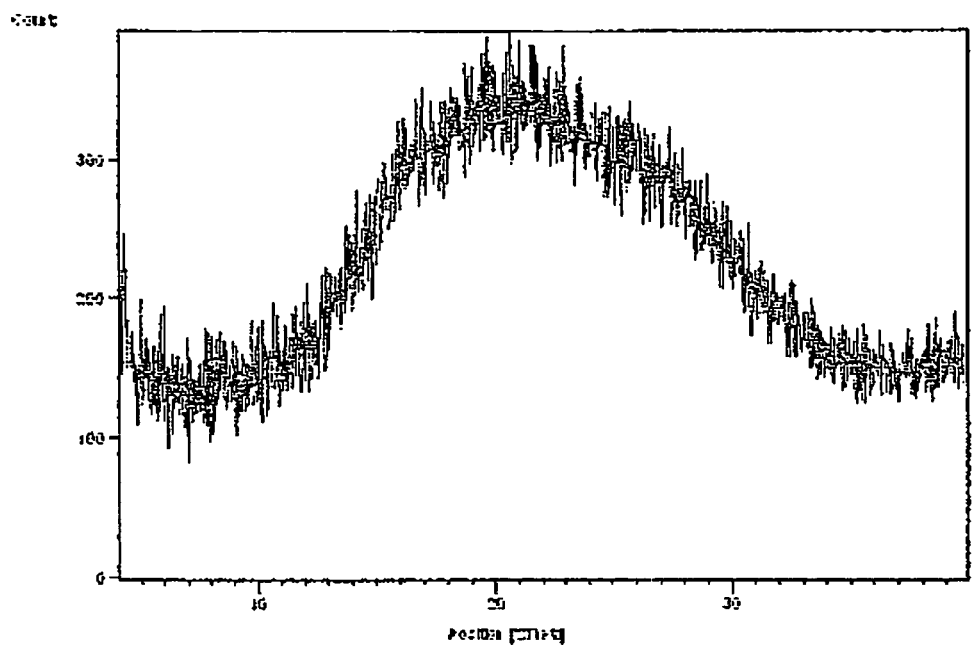
Figure 2. PXRD Diffractogram of Terazosin Hydrochloride
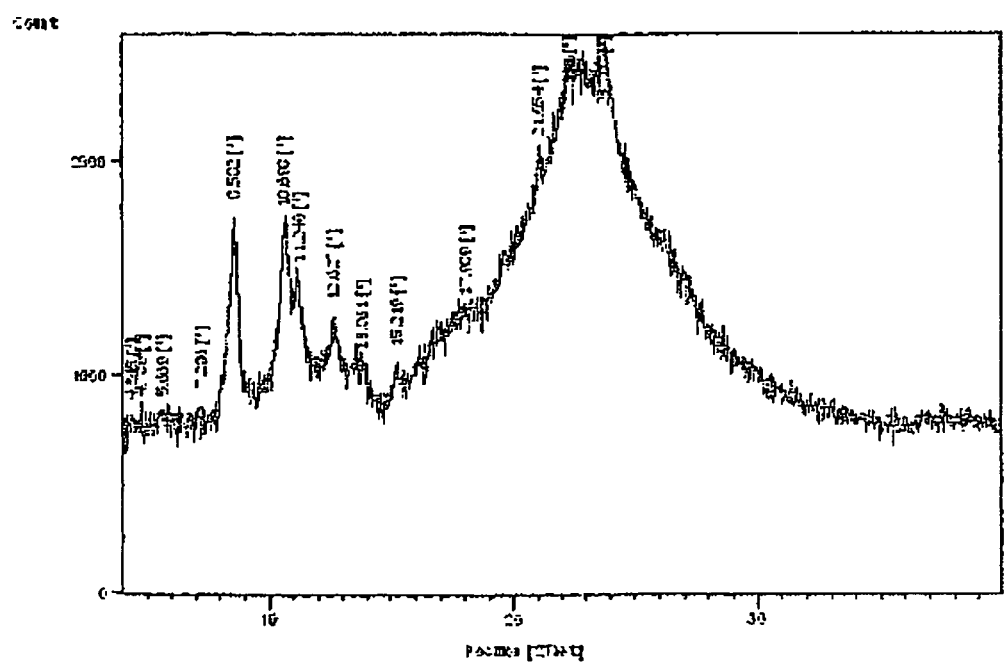

PREPARATION OF ACID ADDITION SALTS OF AMINE BASES BY SOLID PHASE—GAS PHASE REACTIONS

FIELD OF INVENTION

The present invention relates to a new, useful and advantageous technique for the preparation of acid addition salts of organic amines including medicines and intermediates thereof with the proviso that ziprasidone, its acid addition salts and intermediates thereof are excluded by a gas phase/solid phase reaction.

BACKGROUND OF THE INVENTION

Many commercially valuable compounds are isolated as their acid addition salts; for instance their hydrochloride, hydrobromide or acetate salts. This is especially true in the pharmaceutical industry where many pharmaceuticals are marketed in their salt forms. Examples include terazosin hydrochloride (2-[(4-tetrahydro-2-furoyl)-1-piperazinyl]-4-amino-6,7-di-methoxyquinazoline hydrochloride, 1), flecainide acetate (N-(2-piperidinylmethyl)-2,5-bis(2,2,2-trifluoroethoxybenzamide acetate 2) and ranitidine hydrochloride (N-[2-[[[-5-[(dimethylamino)methyl]-2-furanyl]-methyl]thio]ethyl]-N'-methyl-2-nitro-1,1-ethenediamine hydrochloride, 3). Also, other compounds such as domperidone (5-chloro-1-[1-[3-(2,3-dihydro-2-oxo-1H-benzimidazol-yl)-propyl]-4-piperidinyl]-1,3-dihydro-2H-benzimidazol-2-one, 4) are marketed as their free base.

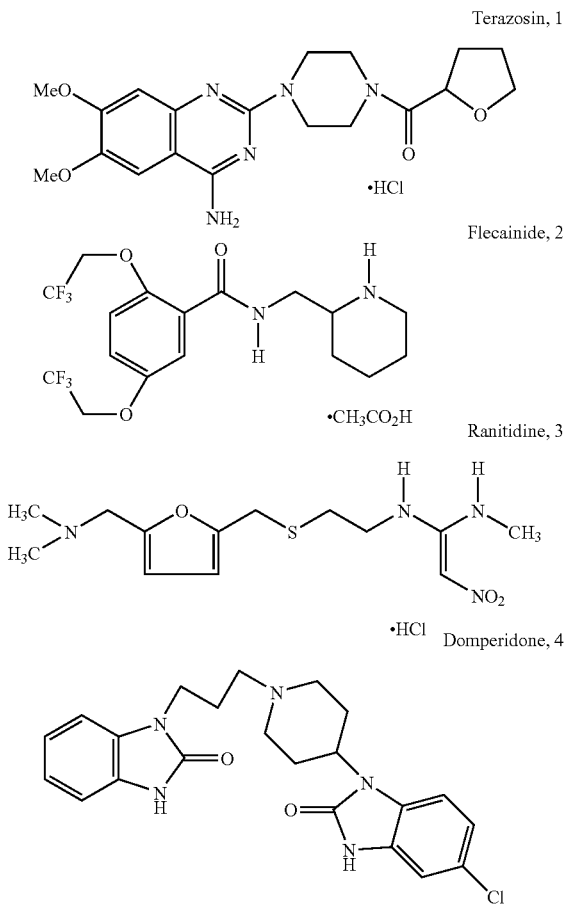

Typically in the prior art, the method of salt formation involved dissolution of the basic compound in a solvent followed by addition of the acid component. However, this would often lead to incorporation of the solvent of dissolution in the acid addition salt upon crystallization or precipitation. Noteworthy is that the preparation of active pharmaceutical ingredients (API's) must meet high purity specifications, for instance in terms of residual solvent content and to this end, regulatory authorities have set out quality guidelines regarding the permissible amounts of residual solvent in active pharmaceutical ingredients (for example, International Conference on Harmonisation, guideline Q3C). In this respect, a dry process (i.e. one which does not employ solvent) for the formation of a hydrochloride, hydrobromide or acetate salt for instance, which would minimize the possibility of residual solvent contamination, would be highly advantageous. The avoidance of solvent also offers an advantage in terms of reduced cost to prepare the product, better reactor throughput due to reduced volumes, and improved safety since many solvents have known toxicities and are flammable. It also represents a more environmentally friendly, or 'green' process.

Kaupp, G., Schmeyers, J. and Boy, J. have reported various types of reactions using gas/solid reactions including the addition of hydrogen halides. This work is reviewed in "Waste-free solid-state syntheses with quantitative yield", *Chemosphere*, Vol. 43 (2001), pp. 55-61. Specifically, Table 1 on page 56 summarizes the types of solid-state reactions examined by Kaupp. A specific example of salt formation on an amino-substrate is found in an earlier publication by Kaupp, G., Pogodda, U. and Schmeyers. J.; namely "Gas/solid Reactions with Acetone", *Chem. Ber.*, (1994), Vol. 127, pp. 2249-2261 where bis-hydrohalide salts of ortho-phenylenediamine substrates were prepared. The highly reactive microcrystalline compounds formed were further reacted with acetone in the gaseous state to form dihydrohalides of their respective 1,5-benzodiazepines by reaction with acetone followed by cyclization and loss of water. Also, an example of hydrohalide salt formation on benzothiazole-substrates is given in Kaupp. G., Lübben, D. and Sauerland, O., "Gas/Solid-Reactions with Sulfur Compounds", *Phosphorus, Sulfur, and Silicon*, (1990), Vol. 53. pp. 109-120).

Thus, the establishment of a novel methods for acid addition salt preparation of commercially important materials such as active pharmaceutical ingredients is desirable.

BRIEF DESCRIPTION OF THE DRAWINGS

FIG. 1 is a Powder X-Ray Diffractogram of Domperidone Hydrochloride.

FIG. 2 is a Powder X-Ray Diffractogram of Terazosin Hydrochloride.

DETAILED DESCRIPTION

SUMMARY

This invention pertains to the development of an original general method for the preparation of acid addition salts including hydrogen chloride, hydrobromide and acetate salts of organic free bases in the absence of solvent(s).

According to one aspect of the invention, there is provided a process for the preparation of an acid addition salt of an organic base, preferably a medicine and intermediates thereof, excluding ziprasidone, its acid addition salts and intermediates thereof, comprising exposing the organic base in solid form to at least one gaseous acid. This results in the formation of acid addition salts in high purity.

According to one aspect of the invention, there is thus provided a process for the manufacture of an acid addition salt of an organic nitrogen base, said process comprising exposing said organic nitrogen base in solid form to an acid in gaseous form.

According to another aspect of the invention, there is provided a process for the manufacture of an acid addition salt of an organic nitrogen base, said process comprising exposing said organic nitrogen base in solid form to an acid in gaseous form wherein the purity of the acid addition salt is substantially the same purity of the organic nitrogen base.

According to yet another aspect of the invention, there is provided a process of forming an acid addition salt of an organic nitrogen base which results in no additional residual solvent introduced during salt formation.

In one embodiment the acid in gaseous form is preferably a halo acid, even more preferably hydrogen chloride or hydrogen bromide.

In another embodiment the acid used in the gaseous state is an organic acid, preferably acetic acid.

According to another aspect of the invention there is provided a process to manufacture an acid addition salt of an organic nitrogen base in a substantially dry environment.

The gaseous acids may include haloacids such as hydrogen chloride (HCl) and hydrogen bromide (HBr) as well as organic acids, preferably weak organic acids, such as acetic acid.

The gaseous acid may comprise neat gas or a mixture of the gaseous acid and one or more inert gases. Examples of inert gases include such as nitrogen, argon and carbon dioxide.

The present invention is useful in the preparation of active pharmaceutical ingredients as hydrogen chloride salts and as the acetate salts. This method is also applicable to other various salts, such as the hydrobromide salts. The present invention is applicable to all organic nitrogen bases.

More importantly, a significant advantage of this method is that the desired salt form of the active pharmaceutical is produced having essentially the same purity as the starting free base. Furthermore, the salt forming step results in no additional residual solvent being introduced as is often the case using the prior art conditions wherein the salt formation is performed in solution by addition of an acid.

Other significant advantages of the instant invention are that it is readily scaleable for industrial production and permits a highly cost-effective process and an intrinsically safer process since it does not require the use of a solvent. The fact that a solvent is not required also permits better reactor utilization.

This method of salt formation is useful to make novel and various polymorphs and forms having improved physical characteristics, for instance size, habit, and bulk density, relative to those obtained by prior art processes.

In a typical procedure according to one aspect of the invention, for forming hydrogen halide addition salts, the free base in solid form is charged into a pressure-withstanding reactor. The reactor is purged with an inert gas, such as nitrogen, for a period of about 1 to 60 minutes, preferably 2 to 10 minutes. The free base is adjusted to a suitable temperature, preferably −50° C. to 40° C. and the nitrogen is replaced with hydrogen halide gas, for instance hydrogen chloride or hydrogen bromide. The reactor is maintained at a pressure in the headspace equal to between about 0.1 to about 3 atm, preferably between about 1 to about 2 atm. The pressure is maintained by continuously supplying the hydrogen halide gas for about 1 to 24 hours duration, preferably 1 to 4 hours. It is preferable gradually to increase the pressure over the course of the reaction, for instance from about 0.1 to about 3 atm. The reaction pressure, temperature and time are chosen to obtain complete or near-complete conversion of the free base to the desired salt while minimizing or preventing the formation of impurities. The duration of the exposure of the free base to the hydrogen halide gas depends on various parameters such as batch size and the specific area of gas-solid contact. After the reaction, the hydrogen halide gas supply is discontinued, and the excess hydrogen halide gas is removed using nitrogen or by vacuum. Preferably, a stream of nitrogen is used for this purpose and the length of time is typically 5 to 120 minutes. The excess hydrogen halide gas is then removed from the product at a suitable temperature and at a suitable pressure, for instance between about 30 and about 100° C. and between about 0.001 and about 0.1 atm, to afford the hydrogen halide salt having the desired molar equivalents of hydrogen halide gas, typically 1.0 equivalents, and a purity higher than 98% per HPLC by area. It is important to note that the excess hydrogen halide gas is recoverable and recyclable, thereby improving the efficiency of the process.

In another embodiment, the free base is charged in an inclined baffled flask that can be rotated through its axis. The flask is rotated to create powder mixing. The advantage of mixing the free base is to reduce the reaction duration significantly by continuously exposing unreacted base to the gaseous acid and to assist in dissipation of heat produced during the salt formation. On the other hand, the benefit of using inert gases is to help dissipate heat generated during the salt forming reaction and also to reduce the rate of reaction.

In another embodiment, the free base is charged in an inclined baffled flask that can be rotated through its axis. A neat inert gas, for instance nitrogen or argon, is bubbled through a liquid organic acid, for instance acetic acid, and then the inert gas is directed towards the mixed free base, thus efficiently taking acetic acid vapour to the free base. This method was useful to the preparation of organic acid addition salts such as acetate salts.

In another embodiment of the invention, the pressure of the acid gas can be gradually increased throughout the reaction in order to minimize impurity formation and decrease reaction time.

Once all the base has reacted, the obtained salt can be dried under a suitable vacuum at a controlled temperature to reduce the amount of acid to the desired value.

Example 1 describes the production of domperidone hydrochloride using this novel method, which has the characterizing PXRD spectrum shown in FIG. 1.

Example 2 describes the production of terazosin hydrochloride using this novel method, which has the characterizing PXRD spectrum shown in FIG. 2.

Examples 3-6 describe the production of ranitidine hydrochloride, flecainide acetate, flecainide hydrochloride, and flecainide hydrobromide, respectively using this novel method.

While the products prepared by this method often have an amorphous form or a largely amorphous form, this does not limit this invention to a method only for the preparation of only amorphous salts.

EXAMPLES

Example 1

Preparation of Domperidone Hydrochloride
(5-chloro-1-[1-[3-(2,3-dihydro-2-oxo-1H-benzimidazol-yl)-propyl]-4-piperidinyl]-1,3-dihydro-2H-benzimidazol-2-one hydrochloride)

To a 500 mL 3-necked baffled flask was added 4 g of 5-chloro-1-[1-[3-(2,3-dihydro-2-oxo-1H-benzimidazol-yl)- propyl]-4-piperidinyl]-1,3-dihydro-2H-benzimidazol-2-one (domperidone free base, 4). The flask was rotated with an electric motor to mix the powder. A stream of hydrogen chloride gas was passed over the powder for 1 hour at which point the hydrogen chloride flow was discontinued and replaced with a stream of nitrogen for about 1 minute. The excess HCl was then removed from the powder in vacuo at 60° C. for 1.5 hours. The product obtained was 5-chloro-1-[1-[3-(2,3-dihydro-2-oxo-1H-benzimidazol-yl)-propyl]-4-piperidinyl]-1,3-dihydro-2H-benzimidazol-2-one hydrochloride having 1 equivalent of hydrogen chloride and characterized by the powder X-Ray diffractogram shown in FIG. 1.

$^1$H NMR (300 MHz, DMSO-$d_6$) δ 1.80-1.95 (m, 2H), 2.05-2.20 (m, 2H), 2.60-2.80 (m, 2H), 3.05-3.25 (m, 4H), 3.55-3.65 (m, 2H), 3.91 (t, J=6.6 Hz, 2H), 4.45-4.60 (m, 1H), 7.00-7.10 (m, 5H), 7.20-7.25 (m, 1H), 7.44 (d, J=8.4 Hz, 1H), 10.19 (br. s, 1H), 10.93 (s, 1H), 11.14 (s, 1H).

Example 2

Preparation of Terazosin Hydrochloride (2-[(4-tetrahydro-2-furoyl)-1-piperazinyl]-4-amino-6,7-di-methoxyquinazoline hydrochloride)

To a 500 mL 3-necked baffled flask was added 5 g of 2-[(4-tetrahydro-2-furoyl)-1-piperazinyl]-4-amino-6,7-di-methoxyquinazoline (terazosin free base, 1). The flask was rotated with an electric motor to mix the powder and a stream of dry nitrogen was passed over the mixed powder for 2 minutes. The flow of nitrogen was replaced with a flow of hydrogen chloride for 45 min. The flow of hydrogen chloride was stopped for 40 minutes and restarted and maintained for an additional 25 minutes. Hydrogen chloride gas was passed over the powder for a further 1 hour after which, the hydrogen chloride flow was discontinued and replaced with a stream of nitrogen for 2 minutes. The excess HCl was then removed from the powder in vacuo at 60° C. over night. The product obtained was 2-[(4-tetrahydro-2-furoyl)-1-piperazinyl]-4-amino-6,7-di-methoxyquinazoline hydrochloride having 1 equivalent hydrogen chloride and characterized by the powder X-Ray diffractogram shown in FIG. 2.

$^1$H NMR (300 MHz, DMSO-$d_6$) δ 1.75-1.90 (m, 2H), 1.95-2.15 (m, 2H), 3.50-4.00 (m, 16H), 4.76 (dd, J=7.4, 5.6 Hz, 1H), 7.50 (s, 1H), 7.74 (s, 1H), 8.70 (s, 1H), 8.91 (s, 1H), 12.22 (s, 1H).

Example 3

Preparation of Ranitidine Hydrochloride (N-[2-[[[-5-[(dimethylamino)methyl]-2-furanyl]-methyl]thio]ethyl]-N'-methyl-2-nitro-1,1-ethenediamine hydrochloride)

To a 500 mL 3-necked baffled flask was added 10 g of 1-[2-[[[-5-[(dimethylamino)methyl]-2-furanyl]-methyl]thio]ethyl]-N'-methyl-2-nitro-1,1-ethenediamine (ranitidine free base, 3). The flask was rotated with an electric motor to mix the powder and a stream of dry nitrogen was passed over the powder for 2 minutes. The flow of nitrogen was discontinued and a flow of hydrogen chloride was passed over the mixed powder for 2 hours. Pure nitrogen was then passed over the powder. The excess hydrogen chloride was then removed from the powder in vacuo at 60° C. overnight. The product obtained was N-[2-[[[-5-[(dimethylamino)methyl]-2-furanyl]-methyl]thio]ethyl]-N'-methyl-2-nitro-1,1-ethenediamine hydrochloride having an HCl content of 1.2 molar equivalents.

$^1$H NMR (300 MHz, DMSO-$d_6$) δ 2.60-2.90 (m, 1H), 3.20-3.60 (m, 2H), 3.87 (s, 2H), 4.32 (s, 2H), 6.35-6.60 (m, 2H), 6.66 (d, J=3.1 Hz, 1H), 7.30-7.70 (m, 1H), 9.80-10-20 (m, 1H), 11.00 (br. s, 1H).

Example 4

Preparation of Flecainide Acetate (N-(2-piperidinyl-methyl)-2,5-bis(2,2,2-trifluoroethoxybenzamide acetate)

To a 500 mL 3-necked baffled flask was added 10 g of N-(2-piperidinylmethyl)-2,5-bis(2,2,2-trifluoroethoxyben-zamide (flecainide free base, 2). The flask was rotated with an electric motor to mix the powder and a stream of dry nitrogen was passed over the mixed powder for 2 minutes. The flow of nitrogen was then bubbled through pure acetic acid and passed over the mixed powder for 15 hours. Pure nitrogen was then passed over the powder. The excess acetic acid was then removed from the powder in vacuo at 60° C. for 16 hr. The product obtained was N-(2-piperidinylmethyl)-2,5-bis(2,2,2-trifluoroethoxybenzamide acetate.

$^1$H NMR (300 MHz, CDCl$_3$) δ 1.35-1.95 (m, 9H), 2.69 (td, J=12.4, 3.3 Hz, 1H), 3.00-3.15 (m, 1H), 3.24 (d, J=12.4 Hz, 1H), 3.35-3.50 (m, 1H), 3.65-3.75 (m, 1H), 4.37 (q, J=8.1 Hz, 2H), 4.49 (q, J=8.1 Hz, 2H), 6.92 (d, J=9.0 Hz, 1H), 7.05 (dd, J=9.1, 3.1 Hz, 1H), 7.54 (d, J=3.1 Hz, 1H), 8.19 (t, J=5.5 Hz, 1H), 8.87 (s, 2H).

Example 5

Preparation of Flecainide Hydrochloride (N-(2-piperidinylmethyl)-2,5-bis(2,2,2-trifluoroethoxybenzamide hydrochloride)

To a 1 l pressure-withstanding reactor equipped with hydrogen chloride inlet and purge valve was added was added 4 g of N-(2-piperidinylmethyl)-2,5-bis(2,2,2-trifluoroethoxybenzamide (flecainide free base, 2). The reactor was sealed and then purged with a stream of nitrogen for 3 minutes. The flow of nitrogen was stopped and the nitrogen inside the reactor was replaced with neat hydrogen chloride at a pressure regulated at 30 psig using a continuous supply of neat hydrogen chloride gas. After 2 hours, the supply of hydrogen chloride was discontinued. After another period of about 2 hours, the hydrogen chloride was released and a stream of nitrogen was passed through the reactor to purge it and to remove some of the excess hydrogen chloride. The remaining excess hydrogen chloride was then removed from the powder in vacuo at 60° C. overnight. The product obtained was N-(2-piperidinylmethyl)-2,5-bis(2,2,2-trifluoroethoxybenzamide hydrochloride having 0.86 molar eq. of hydrogen chloride.

$^1$H NMR (300 MHz, DMSO-$d_6$) b 1.30-1.90 (m, 6H), 2.77 (td, J=12.2, 3.0 Hz, 1H), 2.95-2.10 (m, 1H), 3.18 (d, J=12.4 Hz, 1H), 3.35-3.55 (m, 2H), 4.74-4.83 (m, 4H), 7.15-7.25 (m, 2H), 7.30 (d, J=2.5 Hz, 1H), 8.17 (br. s, 2H), 8.35 (t, J=5.7 Hz, 1H).

Example 6

Preparation of Flecainide Hydrobromide (N-(2-piperidinylmethyl)-2,5-bis(2,2,2-trifluoroethoxybenzamide hydrobromide)

To a 1 l pressure-withstanding reactor equipped with hydrogen bromide inlet and purge valve was added 7 g of N-(2-piperidinylmethyl)-2,5-bis(2,2,2-trifluoroethoxyben-zamide (flecainide free base, 2). hydrogen bromide gas was passed through the reaction for about 1 min to remove the air in the headspace outside the reactor. Then, the reactor was pressurized to a hydrogen bromide pressure of 40 psig and maintained at that level for 50 minutes. The hydrogen bromide supply was stopped. The reactor was kept sealed overnight. After 14 hr, the pressure inside the reactor dropped to 34 psi. The hydrogen bromide gas was then released and the reactor was purged with nitrogen for 20 minutes. The excess hydrogen bromide was then removed from the powder in vacuo at 65-70° C. for about 15 h to afford flecainide hydrobromide having a 1.25 molar equivalent of hydrogen bromide.

$^1$H NMR (300 MHz, DMSO-$d_6$) δ 1.35-2.00 (m, 6H), 2.70-3.00 (m, 1H), 3.15-3.35 (m, 2H), 3.40-3.65 (m, 2H), 4.57-4.90 (m, 4H), 7.15-7.30 (m, 2H), 7.32 (d, J=2.5 Hz, 1H), 8.40 (t, J=7.7 Hz, 1H), 8.50-8.70 (m, 1H), 8.80-8.95 (m, 1H).

While the following provides a detailed description of the preferred embodiments of the invention in the form of the examples given, it is to be understood that the descriptions in the examples are illustrative only of the principles of the invention and not limiting. Furthermore, as many changes can be made to the invention without departing from the scope of the invention, it is intended that all material contained in the examples be interpreted as illustrative of the invention and not in a limiting sense.

The embodiments of the invention in which an exclusive property or privilege is claimed are as follows:

1. A process for the preparation of an acid addition salt of an organic base, which base is a medicine, comprising exposing the organic base in solid form to a gaseous acid at a temperature in the range of from about −50 to about 40° C., wherein reaction occurs between the solid base and the gaseous acid, with the proviso that ziprasidone, and its acid addition salts are excluded.

2. The process of claim 1 wherein the process is solvent free.

3. The process of claim 1 wherein the exposing the organic base in solid form to gaseous acid occurs in a dry environment.

4. The process of claim 1 further comprising agitation.

5. The process of claim 1 wherein the gaseous acid is mixed with one or more inert gases.

6. The process of claim 1 wherein the acid is a hydrogen halide.

7. The process of claim 6 wherein the hydrogen halide is selected from the group consisting of hydrogen chloride and hydrogen bromide.

8. The process of claim 1 wherein the gaseous acid is an organic acid.

9. The process of claim 8 wherein the organic acid is acetic acid.

10. A solvent free process for preparation of an acid addition salt of an organic base, which base is a medicine, comprising exposing, in a dry environment at a temperature in the range of from about −50° C. to about 40° C., the organic base in solid form to a gaseous acid mixed with one or more inert gases; agitating; and removal of excess acid, wherein reaction occurs between the solid base and the gaseous acid, with the proviso that ziprasidone, and its acid addition salts are excluded.

11. The process of claim 10 wherein the excess acid is collected and recycled.

12. The process of any one of claims 1, 3 and 10 wherein the purity of the salt is substantially the same purity as the organic base.

13. The process of any one of claims 1, 3 and 10 wherein the process is conducted in a pressurized reactor.

14. The process of claim 13 wherein the reactor is maintained at a pressure of about 0.1 atm to about 3 atm.

15. The process of claim 14 wherein the pressure is about 1.0 atm to about 2.0 atm.

16. The process of claim 14 wherein the pressure is increased gradually over a period of time.

17. The process of any one of claims 1, 3 and 10 in which the medicine is selected from the group consisting of domperidone, terazosin, ranitidine and flecainide.

18. The process of claim 17 in which the organic base is domperidone.

19. The process of claim 17 in which the organic base is terazosin.

20. The process of claim 17 in which the organic base is ranitidine.

21. The process of claim 17 in which the organic base is flecainide.

22. The process of claim 12 wherein the organic base is a medicine selected from the group consisting of domperidone, terazosin, ranitidine and flecainide.

23. The process of any one of claims 1, 3 and 10 wherein the organic base is an organic nitrogen base.

* * * * *